(12) United States Patent
Taitel et al.

(10) Patent No.: US 12,087,419 B1
(45) Date of Patent: Sep. 10, 2024

(54) METHODS AND SYSTEMS TO IMPROVE PATIENT MEDICATION ADHERENCE

(71) Applicant: WALGREEN CO., Deerfield, IL (US)

(72) Inventors: Michael S. Taitel, Deerfield, IL (US); Ying Mu, Lincolnshire, IL (US); Margaret A. Wonders, Hawthorn Woods, IL (US); John Guoqiang Hou, Lincolnshire, IL (US); Mouna Zamran, Schaumburg, IL (US)

(73) Assignee: WALGREEN CO., Deerfield, IL (US)

( * ) Notice: Subject to any disclaimer, the term of this patent is extended or adjusted under 35 U.S.C. 154(b) by 706 days.

(21) Appl. No.: 17/172,343

(22) Filed: Feb. 10, 2021

(51) Int. Cl.
*G16H 10/60* (2018.01)
*G06N 5/01* (2023.01)
*G16H 20/10* (2018.01)
*G16H 50/30* (2018.01)

(52) U.S. Cl.
CPC .............. *G16H 20/10* (2018.01); *G06N 5/01* (2023.01); *G16H 10/60* (2018.01); *G16H 50/30* (2018.01)

(58) Field of Classification Search
CPC ........ G16H 10/60; G16H 20/10; G16H 50/70; G16H 20/00
See application file for complete search history.

(56) References Cited

U.S. PATENT DOCUMENTS

2021/0358638 A1* 11/2021 Sreenivasan ........... G16H 10/60

FOREIGN PATENT DOCUMENTS

WO    WO-2015013695 A2 *  1/2015  ............. G16H 10/60

OTHER PUBLICATIONS

Gast, Alina, and Tim Mathes. "Medication adherence influencing factors—an (updated) overview of systematic reviews." Systematic reviews 8 (2019): 1-17. (Year: 2019).*

* cited by examiner

*Primary Examiner* — Jason B Dunham
*Assistant Examiner* — Constantine Siozopoulos
(74) *Attorney, Agent, or Firm* — MARSHALL, GERSTEIN & BORUN LLP; Randall G. Rueth (57) ABSTRACT

Methods and systems for improving patient medication adherence by determining when and/or how to intervene with a patient regarding medication adherence are disclosed. An example computer-implemented method for estimating an adherence risk score for a medication taken by a patient includes: receiving, via a network interface from a server configured for determining follow up with patients regarding medication adherence, a request for an adherence risk score for a patient and medication combination, the adherence risk score representing a risk that the patient will not be adherent with taking the medication as prescribed during a time period; obtaining, with one or more processors, pharmacy records for the patient and medication combination; processing the pharmacy records with a machine learning model to determine the adherence risk score; and providing, via the network interface, the adherence risk score to the server.

20 Claims, 7 Drawing Sheets

METHODS AND SYSTEMS TO IMPROVE PATIENT MEDICATION ADHERENCE

FIELD OF THE DISCLOSURE

This disclosure relates generally to therapeutic adherence, and, more particularly, to methods and systems to improve patient medication adherence.

BACKGROUND

There is increasing interest in patient therapeutic adherence (e.g., adherence to taking medications as prescribed for a medical condition) to improve patient health, improve treatment outcome, increase patient satisfaction, reduce costs associated with untreated medical conditions, etc. For example, insurance companies are interested in increasing therapeutic adherence for common medical conditions (e.g., hyperlipidemia, hypertension, diabetes, etc.) that are often preventable, controllable, treatable, etc. with common, affordable, prescribed medications, and whose therapeutic outcome is often negative without adherence with such prescribed medications. Thus, in some examples, insurance companies engage employees and/or third parties (e.g., pharmacies, doctors, nurses, pharmacists, etc.) to track and/or intervene with patients to increase their adherence in taking prescribed medications for such conditions. For example, third parties may track medication adherence through regular contact with a patient, tracking when a patient isn't regularly refilling a prescription and triggering contact with the patient, etc. However, it may be difficult to accurately determine when and/or how to intervene with a patient regarding medication adherence. Thus, there is a need for methods and systems to improve patient medication adherence by determining when and/or how to intervene with a patient regarding medication adherence.

SUMMARY

In an embodiment, a computer-implemented method for estimating an adherence risk score for a medication taken by a patient includes: receiving, via a network interface from a server configured for determining follow up with patients regarding medication adherence, a request for an adherence risk score for a patient and medication combination, the adherence risk score representing a risk that the patient will not be adherent with taking the medication as prescribed during a time period; obtaining, with one or more processors, pharmacy records for the patient and medication combination; processing the pharmacy records with a machine learning model to determine the adherence risk score; and providing, via the network interface, the adherence risk score to the server.

In another embodiment, a system for estimating an adherence risk score for a medication taken by a patient includes: a network interface configured to receive from a server configured for determining follow up with patients regarding medication adherence, a request for an adherence risk score for a patient and medication combination, the adherence risk score representing a risk that the patient will not be adherent with taking the medication as prescribed during a time period, and provide the adherence risk score to the server; a data transformer configured to obtain pharmacy records for the patient and medication combination; and a machine learning model configured to process the pharmacy records with a machine learning model to determine the adherence risk score.

In still another embodiment, a non-transitory, machine-readable storage medium stores instructions that, when executed by one or more processors, cause a machine to: receive, via a network interface from a server configured for determining follow up with patients regarding medication adherence, a request for an adherence risk score for a patient and medication combination, the adherence risk score representing a risk that the patient will not be adherent with taking the medication as prescribed during a time period; obtain pharmacy records for the patient and medication combination; process the pharmacy records with a machine learning model to determine the adherence risk score; and provide, via the network interface, the adherence risk score to the server.

The figures depict embodiments of this disclosure for purposes of illustration only. One skilled in the art will readily recognize from the following discussion that alternate embodiments of the structures and methods illustrated herein may be employed without departing from the principles set forth herein.

In general, the same reference numbers will be used throughout the drawing(s) and accompanying written description to refer to the same or like parts. The figures are not to scale. Connecting lines or connectors shown in the various figures presented are intended to represent example functional relationships and/or physical or logical couplings between the various elements.

DETAILED DESCRIPTION

Reference will now be made in detail to non-limiting examples, some of which are illustrated in the accompanying drawings.

Figure 1:
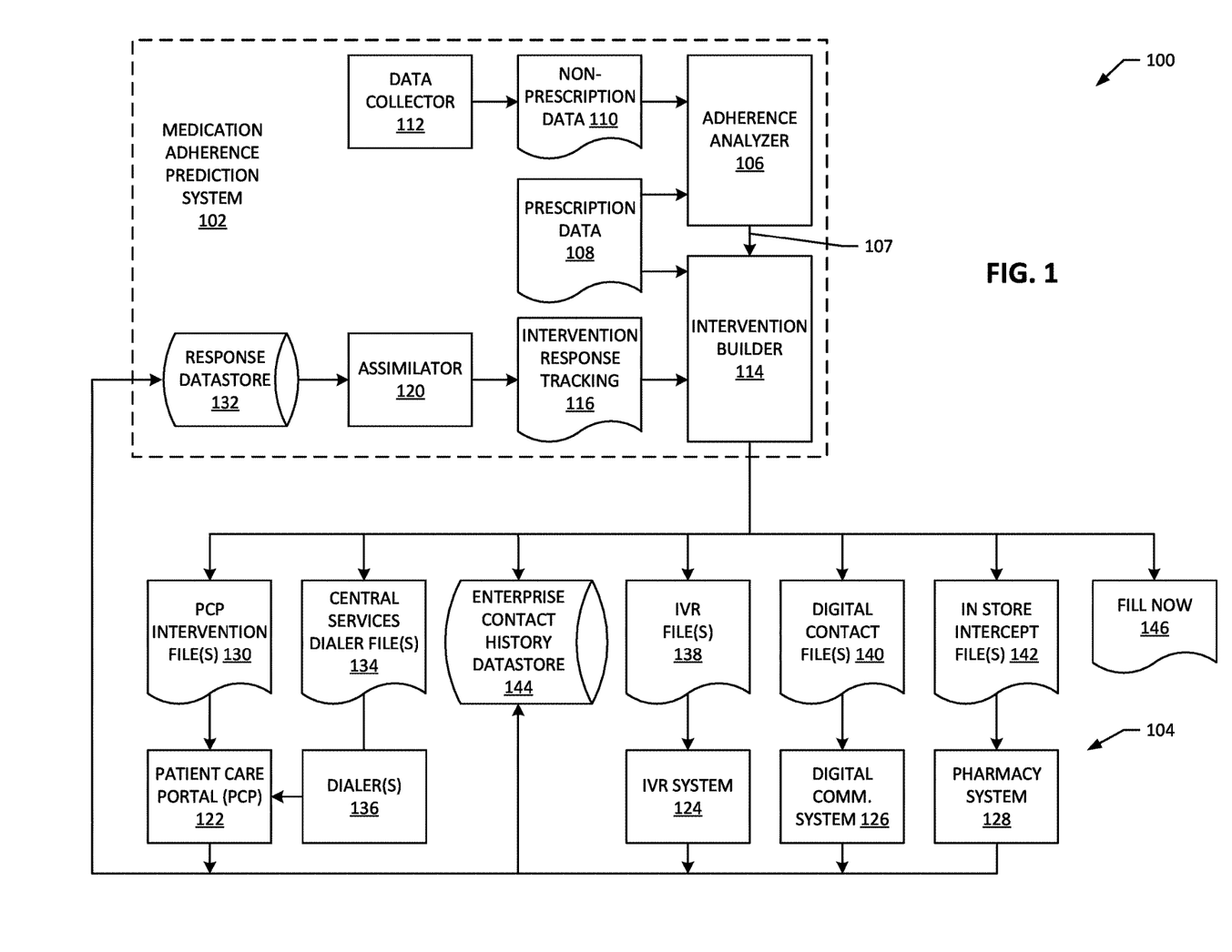
FIG. 1 illustrates an example medication adherence intervention system constructed in accordance with disclosed embodiments, and shown in an example environment of use.

FIG. 1 is a block diagram of example medication adherence tracking system 100 having a medication adherence prediction system 102, and any number and/or type(s) of example interaction systems 104. The medication adherence prediction system 102 includes an adherence analyzer 106 to process (e.g., with a machine learning model) prescription data 108 representing the patient's prescription history or that of other patients for those medication(s) (e.g., when originally filled, when refilled, etc.), etc. to determine an adherence risk score 107. The adherence risk score 107 represents the risk that a patient will not be adherent with their medication(s) for a medical condition during a time period (e.g., during a calendar year). A different adherence risk score 107 may be determined for each of a patient's medical conditions. Likewise, a different adherence risk score 107 may be determined for each medication being used to treat a medical condition. Thus, for example, a patient may be adherent with their treatment for one medical condition and/or medication, while being at risk for being adherent with another medical condition and/or medication. The adherence risk score 107 may be logged with the associated therapeutic class (e.g., medical condition), and the number of gap days (GAP). In some example, the number of GAP days is number of days the patient is believed to have had no medication(s) available to take; GAP may also represent the number of days missed during a period of time.

The prescription data 108 reflects (e.g., on a daily basis), a summarized prescription status for each patient, medication and/or medical condition being tracked for medication and/or medical treatment adherence. Example data included in the prescription data 108 may reflect whether a medication is being automatically refilled (e.g., enrolled an autofill program), whether a patient is enrolled in an intervention program, whether they are enrolled in a program such as the Save a Trip Refills® (SATR) program, how long a prescription has been waiting for pickup, etc.

In some examples, the adherence analyzer 106 additionally processes (e.g., with the machine learning model) non-prescription data 110 representative of non-prescription information associated with a patient, other patients, a pharmacy, geographic region, etc. to determine an adherence risk score. Example non-prescription information includes, but is not limited to, (i) patient's socio-demographic determinants (e.g., of health), (ii) pharmacy location, status, etc., (iii) overall socio-demographic determinants (e.g., of health) for the patients of a pharmacy, (iv) overall socio-demographic determinants (e.g., of health) for residents of a geographic region, or (v) pharmacy sales information, etc.

To collect the non-prescription data 110, the example medication adherence prediction system 102 may include an example data collector 112. The data collector 112 may collect the non-prescription data 110 from any number and/or type(s) of datastores (not shown for clarity of illustration) via any number and/or type(s) of communication paths, networks, application programming interfaces (APIs), etc. The datastores may be owned and/or operated by different entities, and may be accessed according to agreed upon permissions.

The medication adherence prediction system 102 includes an example intervention builder 114 to determine whether, when, why and/or when to contact the patient regarding their adherence with their medication(s) and/or medical treatment(s) based upon adherence risk scores 107, the prescription data 108, and intervention response tracking data 116. The intervention response tracking data 116 being representative of the results of past intervention interactions with a patient regarding one or more medications for a medical condition of interest (e.g., a tracked therapeutic class such as hyperlipidemia, hypertension, diabetes, etc.). When contact is to be made with a patient, the intervention builder 114 directs one or more of the interaction systems 104 to contact the patient regarding their adherence with their medication(s) and/or medical treatment(s). Example interaction systems 104 include, but are not limited to, one or more of a patient care portal (PCP) 122, an interactive voice response (IVR) system 124, a digital communication system 126, a pharmacy system 128, etc.

The medication adherence prediction system 102 may generate one or more PCP intervention files 130 that indicates to operators of the PCPs 122 (e.g., a doctor, nurse, pharmacist, health outcome pharmacist (HOP), etc.) which patients to call in-person regarding which medical condition(s) and/or medication(s). The PCP intervention files 130 may also indication the type of intervention to be performed. For example, to get authorization for a refill, discuss barriers to adherence, etc. In some examples, the PCP intervention files 130 contain contact information, information regarding a patient's medical conditions(s) and/or medication(s), etc. Additionally and/or alternatively, the operators of the PCP 122 may access other database(s) for such information. The operators of the PCP 122 discuss with a patient via telephone their adherence with their medication(s) and/or medical treatments. Intervention information obtained during the telephone call is collected and gathered into a response datastore 132. For example, call disposition (e.g., call completed, unable to contact patient, patient uncooperative, etc.), actions (e.g., (re-)fill prescription, obtain new prescription, etc.), barriers (e.g., insurance, side effects, cost, etc.), notes (e.g., that medication has been discontinued, etc.), etc. When an action is to be taken (e.g., (re-)fill a prescription, obtain a new prescription, etc.), the operator of the PCP 122 can initiate the action via one or more pharmacy fulfillment systems (not shown for clarity of illustration).

In general, the response datastore 132 is a record of all attempted and completed intervention interactions, and their outcome(s). Accordingly, the response datastore 132 may be used, processed, etc. to determine barriers to intervention interactions and/or to identify future intervention interaction types that may be more productive. While a single response datastore 132 is illustrated in FIG. 1, more than one response datastore 132 may be implemented. Further, when an interaction system 104 is a legacy system, it may provide its data to a specific associated legacy response datastore 132 that supports the legacy system. Thus, while all the interaction systems 104 are shown reporting via a single logical path to a single response datastore 132 in FIG. 1 they may, instead, report data via different logical paths.

Information may be stored in the response datastore 132 using any number and/or type(s) of data structures, for example, as raw or unformatted data. The response datastore 132 may be stored on any number and/or type(s) of machine-readable storage medium, devices or disks such as a hard disk drive (HDD), a solid-state drive (SSD), a cache, a flash memory, a read-only memory (ROM), a random access memory (RAM), or any other storage medium, device or storage disk associated with a processor in which information may be stored for any duration (e.g., for extended time periods, permanently, for brief instances, for temporarily buffering, and/or for caching of the information). In some examples, data is initially logged at the interaction systems 104, and collected into the response datastore 132 from the interaction systems 104 on a daily basis. However, other intervals (e.g., as intervention interactions occur) may be used. Moreover, data may be logged directly at the response datastore 132.

In regions where the use of automated dialers is permitted (e.g., based on rules, regulations, laws, policies, etc.), the medication adherence prediction system 102 may generate one or more dialer file(s) 134. Where permitted, automated dialers 136 access the dialer file(s) 134 to determine the next call to initiate, dial the call and, when connected to a live person, presents the call to an operator of the PCP 122 to complete the intervention call.

The medication adherence prediction system 102 may generate one or more IVR files 138 that indicate to the IVR system 124 that certain patients are at high risk for non-adherence. In response to contact being initiated by such a patient, the IVR system 124 offers to connect them to a pharmacist for a live consultation instead of standard automated pharmacy information. The pharmacist interacts with the patient to prompt their medication adherence and obtain information from a patient regarding their adherence with their medication(s) and/or medical treatments. Intervention information obtained during the consultation is entered into the response datastore 132. For example, consultation disposition, actions (e.g., (re-)fill prescription, obtain new prescription, etc.), barriers (e.g., insurance, side effects, cost, etc.), notes (e.g., that medication has been discontinued, etc.), etc. When an action is to be taken (e.g., (re-)fill a prescription, obtain a new prescription, etc.).

The medication adherence prediction system 102 may generate one or more digital contact files 140 that indicate to the digital communication system 126 one or more communication sessions (e.g., electronic mail (email), text message, push notification, etc.) to carry out with a patient regarding their medication and/or medical treatment adherence. The communication sessions may be one-way (e.g., a text message refill reminder, prescription refill past due notification) or interactive (e.g., include option for text response to approve refilling a prescription). Intervention information obtained during the communication session, if any, is collected and gathered into the response datastore 132. For example, communication session disposition (e.g., session completed, unable to contact patient, patient uncooperative, etc.), actions (e.g., (re-)fill prescription, obtain new prescription, etc.), barriers (e.g., insurance, side effects, cost, etc.), notes (e.g., that medication has been discontinued, etc.), etc. When an action is to be taken (e.g., (re-)fill a prescription, obtain a new prescription, etc.), the digital communication system 126 can initiate the action via one or more pharmacy fulfillment systems (not shown for clarity of illustration).

The medication adherence prediction system 102 may generate one or more in-store intercept files 142 that cause the pharmacy system 128 to notify pharmacy personnel when a pharmacist, pharmacy technician, etc. needs to speak with a patient regarding medication and/or medical treatment adherence before a prescription is filled and/or picked up. In some examples, the in-store intercept files 142 contains contact information, information regarding a patient's medical conditions(s) and/or medication(s), etc. Additionally and/or alternatively, the operators of the pharmacy system 128 access other database(s) for such information. The operators of the pharmacy system 128 discuss with a patient their adherence with their medication(s) and/or medical treatments. Intervention information obtained during the conversation is collected and gathered into the response datastore 132. For example, conversation disposition (e.g., conversation completed, patient uncooperative, etc.), actions (e.g., (re-)fill prescription, obtain new prescription, etc.), barriers (e.g., insurance, side effects, cost, etc.), notes (e.g., that medication has been discontinued, etc.), etc. When an action is to be taken (e.g., (re-)fill a prescription, obtain a new prescription, etc.), the operator of the pharmacy system 128 can initiate the action via one or more pharmacy fulfillment systems (not shown for clarity of illustration).

The medication adherence prediction system 102 may generate a prescription fill now file 146 that cause one or more pharmacies to, subject to health plan or payer contracts, (re-)fill certain prescriptions enrolled in autofill (i.e., automatic refills) before their scheduled refill date if a gap has developed between a prior insurance paid data and when the prior prescription was picked up.

In some examples, a historical record of all interventions to be made and/or that have been made via the interaction systems 104 (e.g., any of the PCP 122, the IVR system 124, the digital communication system 126, the pharmacy system 128, etc.) are logged in an enterprise contact history datastore 138.

While example interaction systems 104 are shown in FIG. 1, one or more of the interaction systems 104 illustrated in FIG. 1 may be combined, divided, re-arranged, omitted, eliminated and/or implemented in any other way. Further, one or more interaction systems 104 in addition to, or instead of, those illustrated in FIG. 1 may be implemented. Further still, more than one of any or all of the illustrated interaction systems 104 may be implemented.

To generate the intervention response tracking data 116, the example medication adherence prediction system 102 includes an example assimilator 120. The assimilator 120 processes the daily raw or unformatted intervention response data stored in the response datastore 132 to form formatted intervention response tracking data 116. The intervention response tracking data 116 may be formed on a daily basis. Intervention disposition information stored in the intervention response tracking data 116 may be classified at the patient level (e.g., patient refilled prescription, etc.) and/or global product identifier (GPI) level (e.g., therapy discontinued, prescription changed, etc.). A disposition may include an assigned number of days in which the patient will not be contacted again.

While the example medication adherence prediction system 102 and/or, more generally, the example medication adherence tracking system 100 to improve patient medication adherence are illustrated in FIG. 1, one or more of the elements, processes, devices and/or systems illustrated in FIG. 1 may be combined, divided, re-arranged, omitted, eliminated or implemented in any other way. Further, the medication adherence prediction system 102 and/or, more generally, the medication adherence tracking system 100 may include one or more elements, processes, devices and/or systems in addition to, or instead of, those illustrated in FIG. 1, or may include more than one of any or all of the illustrated elements, processes, devices and/or systems.

Figure 2:
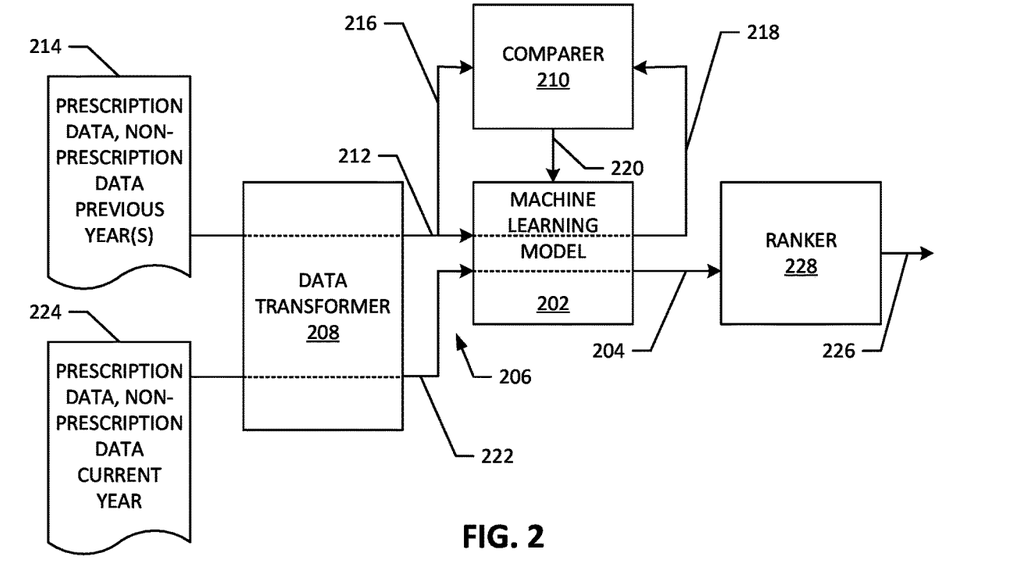
FIG. 2 is a block diagram illustrating an example implementation of the adherence analyzer of FIG. 1, in accordance with disclosed embodiments.

FIG. 2 is a block diagram of an example adherence analyzer 200 that may be used to implement the adherence analyzer 106 of FIG. 1. The example adherence analyzer 200 includes an example machine learning model 202 to determine adherence risk scores 204 based on prescription data (e.g., the prescription data 108) and non-prescription data (e.g., the non-prescription data 110). The machine learning model 202 may be a statistical model such as a multinomial logistic regression model, a decision tree, a gradient boosting model, a random forest model, a logistic regression model, etc. The adherence risk scores 204 may be logged with an associated therapeutic class (e.g., medical condition such a diabetes, hyperlipidemia, hypertension, etc.), and number of GAP days (e.g., number of days patient is believed to have had no medication(s) to take).

To form input data 206 for the machine learning model 202, the adherence analyzer 200 includes an example data transformer 208.

Figure 3:
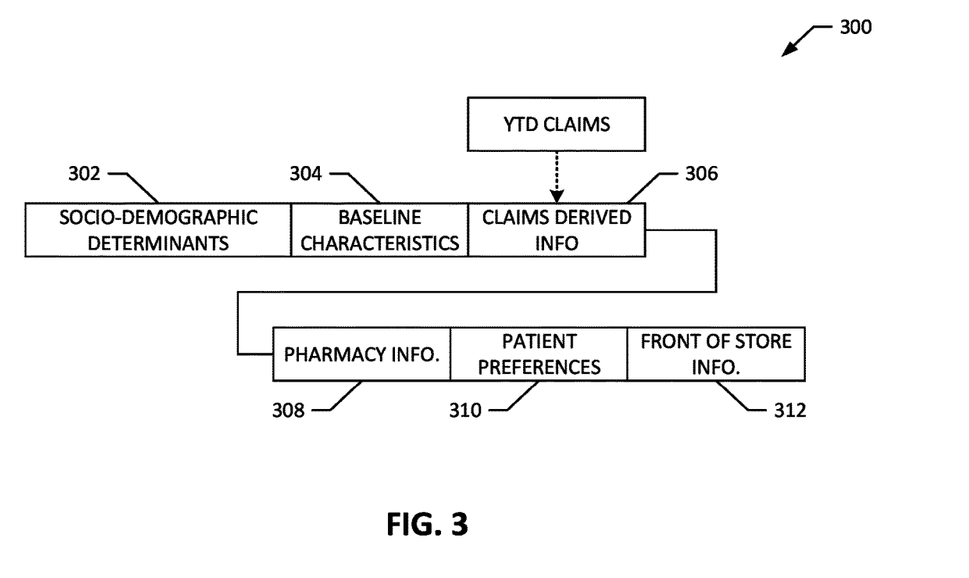
FIG. 3 illustrates an example data structure that may be formed by the data transformer of FIG. 2 as an input vector for the machine learning model of FIG. 2.

FIG. 3 illustrates an example data structure 300 that may be used to form vectors of the input data 206 for a patient and medication combination for the machine learning model 202. The data transformer 208 extracts, obtains, accesses, processes, etc. prescription and non-prescription data for a patient and medication combination to form vectors of the input data 206 according to the data structure 300. In the illustrated example of FIG. 3, a vector 300 of input data 206 includes:

- one or more fields 302 that include socio-demographic determinants for a patient, for example:
  - race/ethnicity
  - income
  - own/rent residence
  - employment status, etc.
- one or more fields 304 including baseline prescription characteristics, for example:
  - medication adherence history in terms of proportional days covered (PDC), which is the number of days a patient has medication on hand in a measurement period divided by the number of days in the measurement period,
  - GAP pattern (e.g., always pick up medication five days late),
  - comorbidities,
  - complexity of therapy (e.g., medications to treat diabetes),
  - copay amount, etc.
- one or more fields 306 that represent prescription claims information, for example:
  - first month medication filled,
  - number of times medication has been filled,
  - number of days supply per fill,
  - percent of fills that are 90-day fills,
  - number of medications taken for targeted therapeutic class,
  - days late or early for the first fill,
  - number of refills remaining,
  - copay amount, etc.
- one or more fields 308 that represent pharmacy/store information, for example:
  - rural/urban,
  - amount of yearly sales,
  - operation hours,
  - local socio-demographic determinants, etc.
- one or more fields 310 that represent patient preferences, for example:
  - program enrollments,
  - barriers to medication adherence,
  - responsiveness of patient to various intervention interaction methods, etc.
- one or more fields 312 that represent non-pharmacy sales information, for example:
  - amount of non-pharmacy sales,
  - amount of pharmacy sales,
  - over-the-counter medication utilization,
  - sales by retail segment or part of store, etc.

While an example data structure 300 that may be used to form vectors of the input data 206 for the machine learning model 202 is illustrated in FIG. 3 and described herein, one or more of the fields illustrated in FIG. 3 and described herein may be combined, divided, re-arranged, omitted, eliminated and/or implemented in any other way. Further, the example data structure 300 may include one or more fields in addition to, or instead of, those illustrated in FIG. 3 and described herein, and/or may include more than one of any or all of the illustrated and/or described fields.

Returning to FIG. 2, to train the machine learning model 202, the adherence analyzer 200 includes a comparator 210. When the machine learning model 202 is being trained, the data transformer 208 forms input data 212 for patient and medication combinations from prescription and non-prescription data 214 for one or more previous years, for a therapeutic class or medication, and for multiple patients, wherein each vector of the input data 212 has a corresponding known or previously determined medication adherence outcomes 216 (e.g., representing whether they were adherent or nonadherent). The machine learning model 202 processes each vector of the input data 212 to determine a respective adherence risk score 218. The comparator 210 determines (e.g., computes) differences 220 between the known medication adherence outcomes 216 and the adherence risk scores 218. The machine learning model 202 is updated based upon the differences 220 using, for example, predictive modeling.

In some examples, the machine learning model 202 is trained with a portion (e.g., half) of the data 214, as described above, and the remaining data 214 is used to verify the machine learning model 202. In some examples, the machine learning model 202 is trained more than once with the portion of the data 214. To verify the machine learning model 202, the remaining data 214 is processed by the machine learning model 202 and a sum of squares, or some other statistical metric of the errors 220 may be computed and used to determine when the performance of the machine learning model 202 is no longer improving through further training with the portion of the data 214.

In use (e.g., once a week), the data transformer 208 forms a vector 222 of input data 206 from prescription and non-prescription data 224 for a current year, for a therapeutic class and/or medication, and for a particular patient. The machine learning model 202 processes the vector 222 of input data to determine an adherence risk score 204 for the patient, for the therapeutic class and/or medication (i.e., for a patient and medication combination).

To form a ranked list 226 of patient/medication/therapeutic class combinations that are most likely to be able to be made to be adherent, the adherence analyzer 200 includes a ranker 228. The example ranker 228 may queue the adherence risk scores 204 for a plurality of patient/medication/therapeutic class combinations, and then sort or rank them based upon the adherence risk scores 204. By ranking the patient/medication/therapeutic class combinations based upon their adherence risk scores 204, the intervention builder 114 (see FIG. 1) can target for intervention those patient/medication/therapeutic class combinations that can be most likely be brought into adherence through intervention.

While an example manner of implementing the adherence analyzer 106 of FIG. 1 is illustrated in FIG. 2, one or more of the elements, processes and/or devices illustrated in FIG. 2 may be combined, divided, re-arranged, omitted, eliminated and/or implemented in any other way. Further, the machine learning model 202, the data transformer 208, the comparer 210, the ranker 228 and/or, more generally, the adherence analyzer 200 of FIG. 2 may be implemented by hardware, software, firmware and/or any combination of hardware, software and/or firmware. Thus, for example, any of the machine learning model 202, the data transformer 208, the comparer 210, the ranker 228 and/or, more generally, the adherence analyzer 200 could be implemented by one or more of an analog or digital circuit, a logic circuit, a programmable processor, a programmable controller, a graphics processing unit (GPU), a digital signal processor (DSP), an application specific integrated circuit (ASIC), a programmable logic device (PLD), a field programmable gate array (FPGA), and/or a field programmable logic device (FPLD). When reading any claim of this patent to cover a purely software and/or firmware implementation, at least one of the machine learning model 202, the data transformer 208, the comparer 210, the ranker 228 and/or, more generally, the adherence analyzer 200 is/are hereby expressly defined to include a non-transitory, machine-readable storage medium, device or disk. Further still, the example adherence analyzer 200 of FIG. 2 may include one or more elements, processes and/or devices in addition to, or instead of, those illustrated in FIG. 2, and/or may include more than one of any or all of the illustrated elements, processes and devices.

Figure 4:
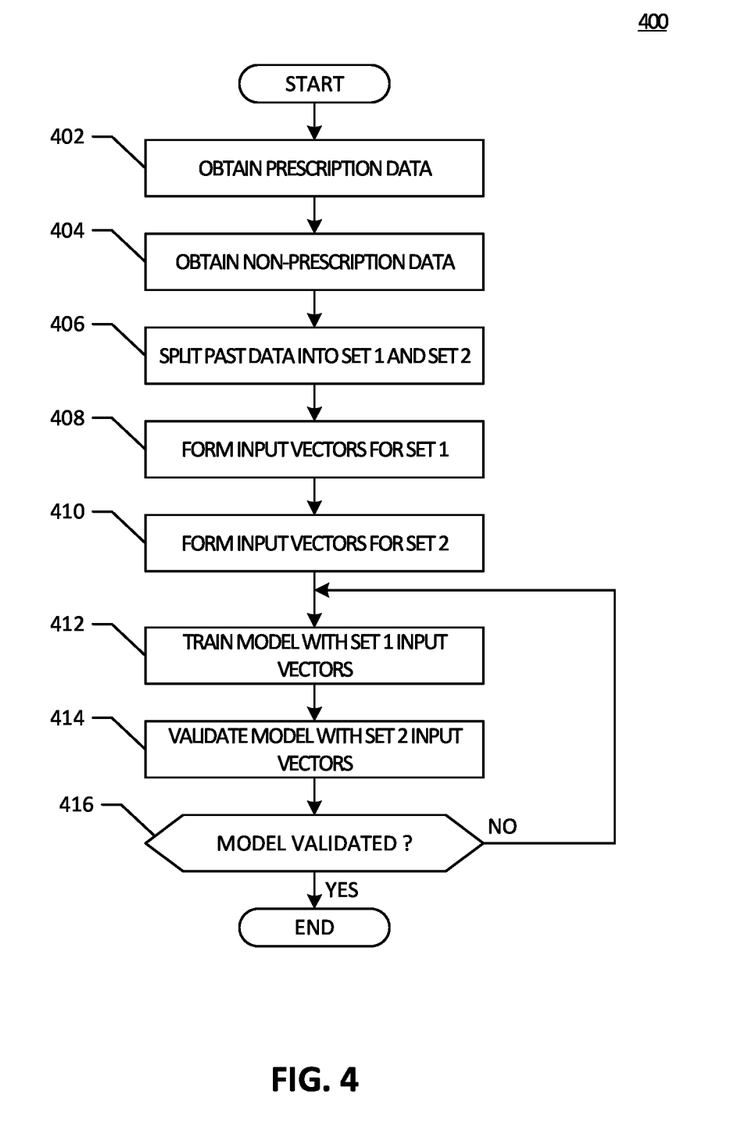
FIG. 4 is a flowchart representative of an example method, hardware logic and/or machine-readable instructions for training and validating the machine learning model of FIG. 2, in accordance with disclosed embodiments.
Figure 5:
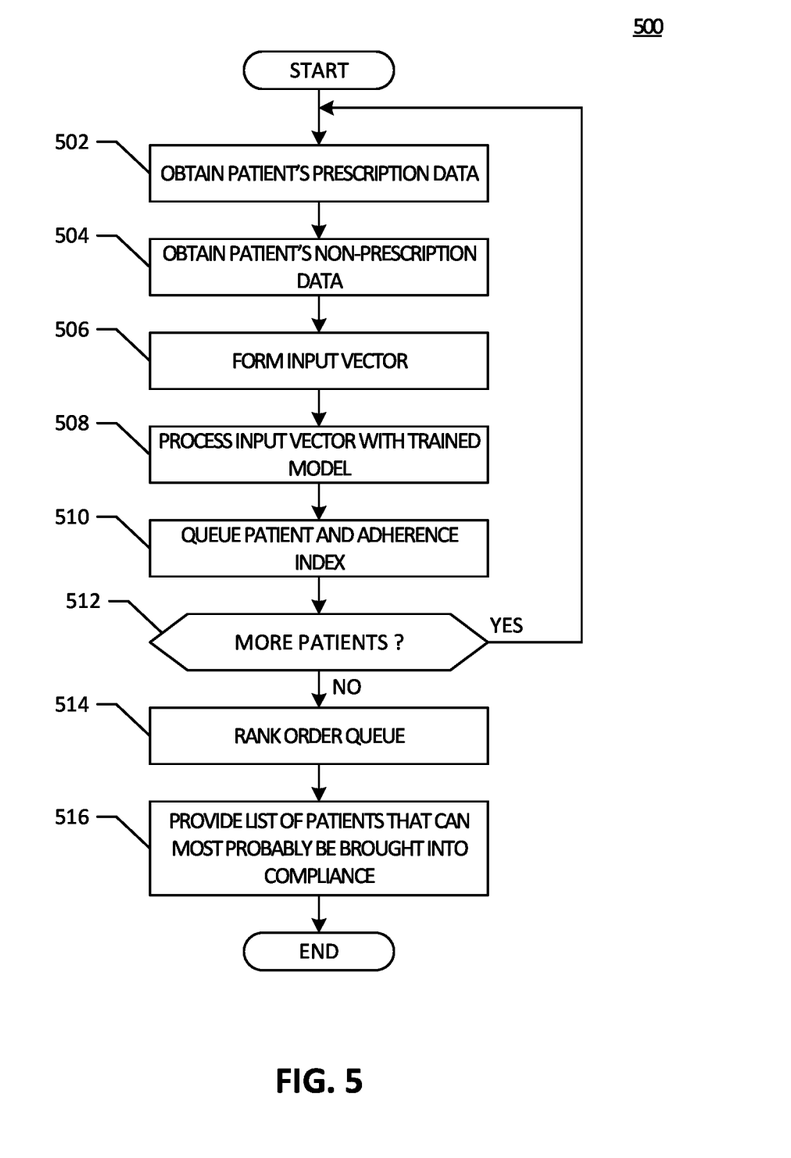
FIG. 5 is a flowchart representative of an example method, hardware logic and/or machine-readable instructions for determining adherence risk scores using the example machine learning model of FIG. 2, in accordance with disclosed embodiments.

FIGS. 4 and 5 illustrate flowcharts 400 and 500 representative of example processes, methods, software or machine-readable instructions, etc. for implementing the adherence analyzer 200 of FIG. 2. The processes, methods, software and machine-readable instructions may be an executable program or portion of an executable program for execution by a processor such as the processor 802 of FIG. 8. The program may be embodied in software or machine-readable instructions stored on a non-transitory, machine-readable storage medium such as an HDD, an SDD, a cache, a flash memory, a ROM, a RAM, or any other storage medium, device or storage disk associated with the processor 802 in which information is stored for any duration (e.g., for extended time periods, permanently, for brief instances, for temporarily buffering, and/or for caching of the information). Further, although example programs are described with reference to the flowcharts 400 and 500, many other methods of implementing the adherence analyzer 200 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an ASIC, a PLD, an FPGA, an FPLD, a logic circuit, etc.) structured to perform the corresponding operation without executing software or instructions.

The example flowchart 400, which may be used to train the machine learning model 202 of FIG. 2, begins with the data transformer 208 obtaining, accessing, etc. prescription data (e.g., the prescription data 108) (block 402) and non-prescription data (e.g., the non-prescription data 110) (block 404). The data transformer 208 splits past data (e.g., for a previous year) into two sets, set 1 and set 2 (block 406). The data may be split randomly. The data transformer 208 forms vectors 212 of input data 206 corresponding to set 1 and set 2 (blocks 406 and 408, respectively).

The machine learning model 202 is trained using the vectors 212 of set 1 of the input data 206 based upon differences between known medication adherence outcomes 216 corresponding to the vectors 212 of input data 206 for set 1, and adherence risk scores 218 determined by the machine learning model 202 using, for example, predictive modeling, multinomial logistic regression, a decision tree, a gradient boost model, a logistic regression model, etc. (block 412).

The vectors 212 of input data 206 for set 2 are used to verify the machine learning model 202 (block 414). If the machine learning model 202 is verified (block 416), control exits from the example flowchart 400 of FIG. 4. Otherwise, control returns to block 412 to repeat training of the machine learning model 202.

The example flowchart 500, which may be used to compute adherence risk scores 204 using the machine learning model 202 of FIG. 2, begins with the data transformer 208 obtaining, accessing, etc. for a presently considered patient/medication(s)/therapeutic class combination, prescription data (e.g., the prescription data 108) (block 502) and non-prescription data (e.g., the non-prescription data 110) (block 504). The data transformer 208 forms an input vector 222 of input data 206 based on the accessed data (block 506). The machine learning model 202 processes the input vector 222 to determine an adherence risk score 204 (block 508). The ranker 228 queues the patient/medication(s)/therapeutic class, adherence risk score combination (block 512). If there are more patient/medication(s)/therapeutic class combinations to process, control returns to block 502.

Otherwise, the ranker 228 ranks the patient/medication(s)/therapeutic class combinations based upon, for example, their adherence risk scores 204 (block 514), and provides the ranked list to the intervention builder 114 (see FIG. 1) (block 516). Control then exits from the example flowchart 500.

Figure 6:
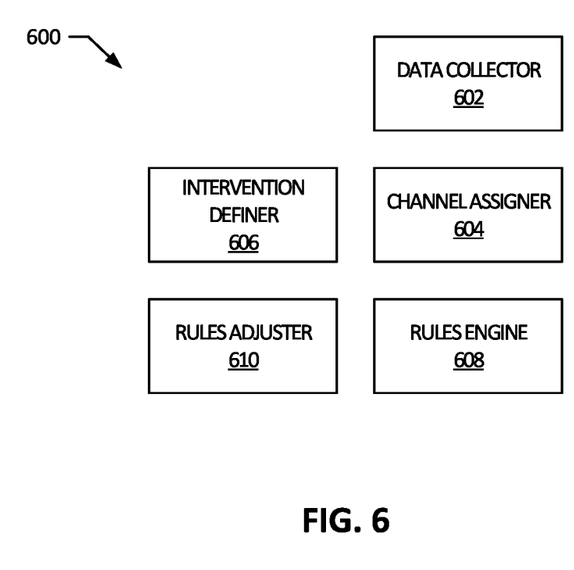
FIG. 6 is a block diagram illustrating an example implementation of the intervention builder of FIG. 1, in accordance with disclosed embodiments.

FIG. 6 is a block diagram illustrating an example intervention builder 600 that may be used to implement the example intervention builder 114 of FIG. 1, in accordance with disclosed embodiments. To collect data for processing, the example intervention builder 600 includes an example data collector 602. The data collector 602 access, obtains, etc. the intervention response tracking data 116 and/or the prescription data 108. Additionally, the data collector 602 may apply one or more pre-defined filters to remove inapplicable data. For example, data associated with deceased persons, non-included persons, pets, minors, those removed a medication adherence program based on previous contact(s), people recently contacted by a HOP, etc.

To assign patients to intervention channels via, for example, one of the interaction systems 104, the example intervention builder 600 includes an example channel assigner 604. The example channel assigner 604 assigns a patient to one or more of the interaction systems 104 based on, for example, their past response(s) to the interaction systems 104. For example, a patient who is responsive to refill reminders via a text message are assigned to the digital communication system 126 for a text-based intervention, a patient who is unresponsive to the IVR system 124 may be assigned to text-based intervention instead, etc.

To provide information, data, etc. for the intervention files 130, 134, 138, 140, 142 and/or 144, the example intervention builder 600 includes an example intervention definer 606. The intervention definer 606 collects and provides the data necessary for the assigned intervention system 104 to attempt to intervene with the patient. For example, for a text message intervention, the intervention definer can provide information representing the patient, their contact information, the name of the prescription medication, and a refill due date.

To determine whether to, additionally and/or alternatively, intervene with a telephone call from a live person, e.g., a HOP, the example intervention builder 600 includes an example rules engine 608. The rules engine 608 applies one or more rules that determine whether intervention by a live person is appropriate and, if appropriate, what type(s) of intervention (e.g., encourage a proactive refill, encourage a refill for a past due refill, discuss barriers to treatment, etc.) are to occur. In some examples, the rules are defined as macros. In some examples, the rules and/or the order in which they are applied vary based on insurer, payor, contract and/or other bases.

A proactive refill type of intervention is a proactive approach to a patient's needed refills. The goal is to refill the medication for the patient before they develop a gap in care so the patient never misses a day of therapy. Example rules that result in an intervention by a HOP for a proactive refill type of intervention include, but are not limited to:

Rule 1: Refill is due between the next 1 and X days and is not already in the bin for pickup. The prescription is not enrolled in SATR or autofill, and the patient is not receiving refill reminders. X is defaulted to 7 but configurable.

Rule 2: Refill is due between the next 1 and X days and is not already in the bin for pickup. The patient is receiving refill reminders. The intervention is limited to patients with less than X gap days remaining.

Rule 3: Same as Rule 2 but intervene for a gap days remaining between X+1 and Z (X is defined in Rule 2 and Z is the maximum allowed gap days).

A delayed therapy type of intervention is designed to identify patients that have not yet filled their medication and have developed a gap in care. The goal is to refill the identified medication, if appropriate for the patient. Example rules that result in an intervention by a HOP for a delayed therapy type of intervention include, but are not limited to:

Rule 4: Refill is late by 8 days or more, and is not already in the bin for pickup.

Rule 5: Refill is late by 3-7 days and is not already in the bin for pickup. Autofill and SATR enrolled prescriptions are excluded.

A barrier review type of intervention is an in-depth discussion around the medications of a specific disease state (hypertension, diabetes, or cholesterol) for a patient. This intervention explores barriers the patient may be having to adherence and encourages the pharmacist to offer solutions to resolve the identified barriers. Example rules that result in an intervention by a HOP for a barrier review type of intervention include, but are not limited to:

Rule 6: Patient is not late to refill and does have a refill due in the next 7 days.

Rule 7: Patient is new (e.g., no evidence of script filled in prior calendar review), or not signed up for any service that would initiate a refill (no refill reminders, not on SATR, not enrolled in autofill, etc.).

A 90 day conversion type of intervention may be added if patient qualifies for one or more of the interventions above, their health plan contract allows 90 day (re)fills, and patient is not receiving 90 day refills now or has not in past 90 days. Patient's notes are scanned for an indication they have rejected 90 day refills (e.g. "30 day only", "no 90 day").

In some examples, the rules, the order in which they are applied and/or parameters of the rules (e.g., the parameters X and Z above) may vary in response to the resource load of, for example, the PCP 122. To adjust the rules, the order in which they are applied and/or parameters of the rules, the example intervention builder 600 includes a rules adjuster 610. The rules adjuster 610 may adjust the rules based on, for example, resource load. For example, if the PCP 122 can handle 100 calls in the next week, but the rules results in 150 patients flagged for contact by a HOP, the rules adjuster 610 can adjust the rules, the order in which they are applied and/or parameters of the rules to reduce the number of flagged patients. Similarly, if the PCP 122 can handle 100 calls in the next week, but the rules results in 50 patients flagged for contact by a HOP, the rules adjuster 610 can adjust the rules, the order in which they are applied and/or parameters of the rules to increase the number of flagged patients. The rules adjustor 610 preprocesses the rules to evaluate the qualifying population and compares to the available licensed staff per location. The rules adjustor 610 reprocesses based on non-adherence risk score, number of gap days and payor contract priority to set the call/patient thresholds per location.

For patients identified for an intervention by a HOP based on one or more (potentially adjusted) rules, the intervention definer 606 provides the necessary data and/or information for the PCP intervention file(s) 130 in the form of, for example, a list of persons to be contacted by a HOP and their associated information.

While an example manner of implementing the intervention builder 114 of FIG. 1 is illustrated in FIG. 6, one or more of the elements, processes and/or devices illustrated in FIG. 6 may be combined, divided, re-arranged, omitted, eliminated and/or implemented in any other way. Further, the data collector 602, the channel assigner 604, the intervention definer 606, the rules engine 608, the rules adjuster and/or, more generally, the intervention builder 600 of FIG. 6 may be implemented by hardware, software, firmware and/or any combination of hardware, software and/or firmware. Thus, for example, any of the data collector 602, the channel assigner 604, the intervention definer 606, the rules engine 608, the rules adjuster and/or, more generally, the intervention builder 600 could be implemented by one or more of an analog or digital circuit, a logic circuit, a programmable processor, a programmable controller, a GPU, a DSP, an ASIC, a PLD, an FPGA, and/or a FPLD. When reading any claim of this patent to cover a purely software and/or firmware implementation, at least one of the data collector 602, the channel assigner 604, the intervention definer 606, the rules engine 608, the rules adjuster and/or, more generally, the intervention builder 600 is/are hereby expressly defined to include a non-transitory, machine-readable storage medium, device or disk. Further still, the example intervention builder 600 of FIG. 6 may include one or more elements, processes and/or devices in addition to, or instead of, those illustrated in FIG. 6, and/or may include more than one of any or all of the illustrated elements, processes and devices.

Figure 7:
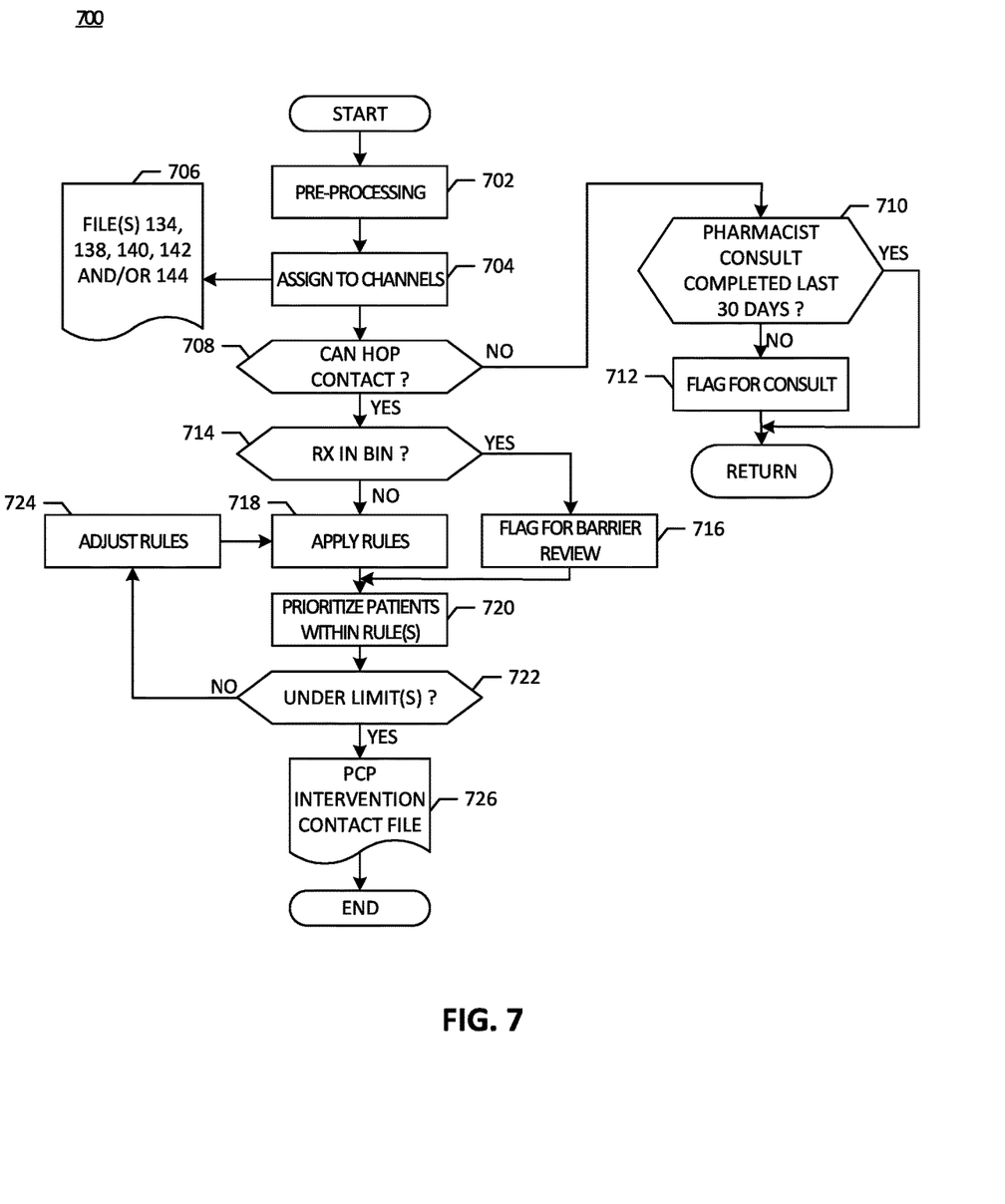
FIG. 7 is a flowchart representative of an example method, hardware logic or machine-readable instructions for implementing the example intervention builder of FIGS. 1 and/or 6, in accordance with disclosed embodiments.

FIG. 7 is a flowchart representative of an example method, hardware logic or machine-readable instructions for implementing the example intervention builders 114, 600 of FIGS. 1 and/or 6, in accordance with disclosed embodiments. The machine-readable instructions may be an executable program or portion of an executable program for execution by a computer processor such as the processor 802 shown in the example processor platform 800 discussed below in connection with FIG. 8. The program may be embodied in software stored on a non-transitory, machine-readable storage medium such as an HDD, an SDD, a cache, a flash memory, a ROM, a RAM, or any other storage medium, device or storage disk associated with the processor 802 in which information is stored for any duration (e.g., for extended time periods, permanently, for brief instances, for temporarily buffering, and/or for caching of the information). Further, although example program is described with reference to the flowchart 7, many other methods of implementing the intervention builders 114, 600 of FIGS. 1 and/or 6 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an ASIC, a PLD, an FPGA, an FPLD, a logic circuit, etc.) structured to perform the corresponding operation without executing software or instructions.

The example flowchart of FIG. 7 begins with the intervention builder 114, 600 (e.g., the data collector 602) collecting and/or preprocessing the prescription data 108 and/or the intervention response tracking data 116 (block 702). The intervention builder 114, 600 (e.g., the channel assigner 604) assigns patients to intervention channels (block 704). The intervention builder 114, 600 (e.g., the intervention definer 606) provides the necessary input for the files 134, 138, 140, 142 and/or 144 for the interaction system(s) 104.

If a particular patient cannot be contact by a HOP (block 708), the channel assigner 604 determines whether a pharmacy consult by a local pharmacist for the patient has occurred in the past thirty days (block 710). If so, the patient is not considered for intervention by a HOP or pharmacist. If a pharmacy consult has not occurred in the last thirty days (block 710), the patient is identified in an in-store intercept file 142 for a consult with the local pharmacist (block 712).

Returning to block 708, if a particular patient can be contacted by a HOP (block 708), and the patient already has a prescription that has been waiting more than D days in a bin for pickup (block 714), the patient is flagged for a barrier review type of HOP intervention (block 716). Otherwise, the intervention builder 114, 600 (e.g., the rules engine 608) applies one or more rules that determine whether intervention by a live person (e.g., a HOP) is appropriate for a particular patient and, if appropriate, what type(s) of intervention (e.g., encourage a proactive refill, encourage a refill for a past due refill, discuss barriers to treatment, etc.) are to occur (block 718).

Once all patients have been assigned to one or more intervention channels at block 704, 712, 716 and/or 718, the patients assigned to each intervention type are prioritized based on, for example, their adherence risk scores 107, 204 (e.g., those who can mostly likely be made are prioritized), # of therapeutic classes a patient belongs to, and/or their number of gap days (block 720).

If there are more patients flagged for HOP intervention than available HOP resources can handle (block 722), the invention builder 114, 600 (e.g., the rules adjuster 610) adjust the rules, the order in which they are applied and/or parameters of the rules to reduce or increase the number of patients flagged for HOP intervention at blocks 716 and 718 (block 724).

For patients identified for an intervention by a HOP as described above, the intervention definer 606 provides the necessary data and/or information for the PCP intervention file(s) 130 in the form of, for example, a list of persons to be contacted by a HOP and their associated information (block 726)

Figure 8:
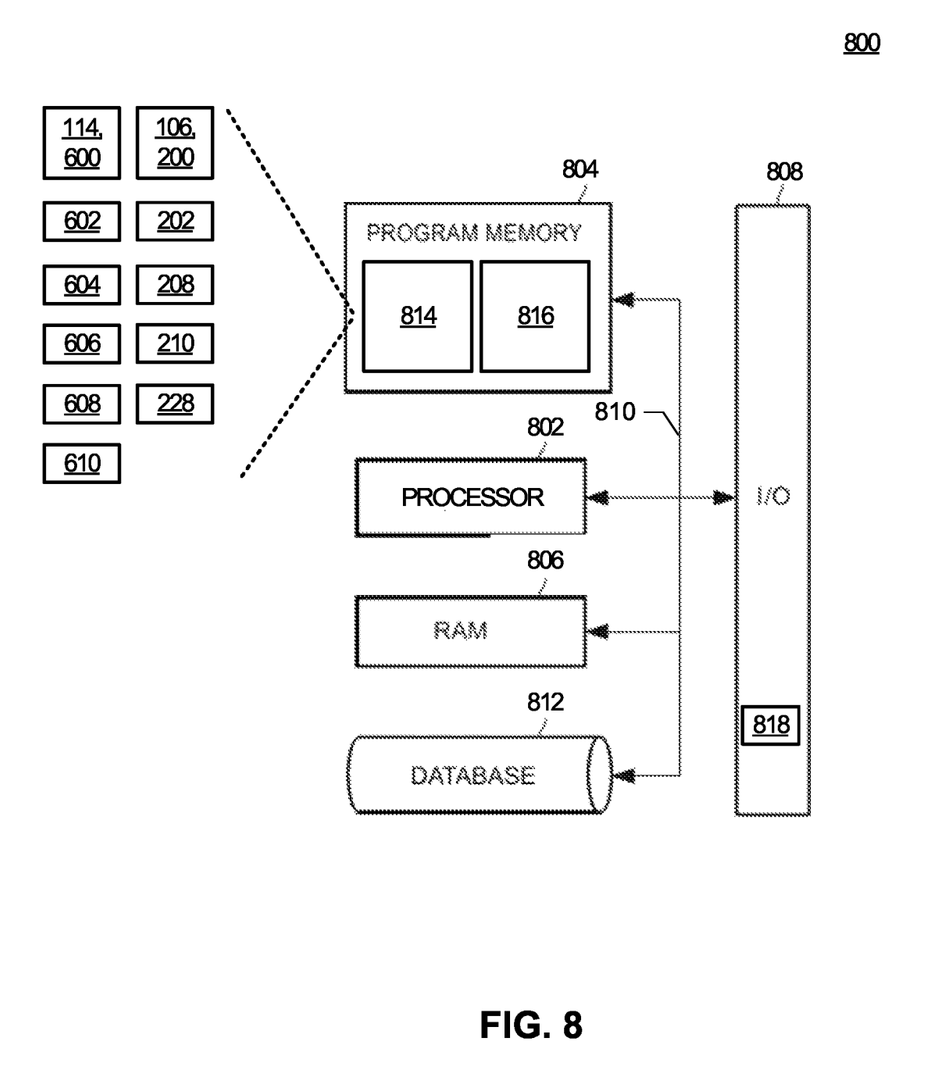
FIG. 8 is a block diagram of an example computing system to implement the various user interfaces, methods, functions, etc., for capturing images of damage and calculating damage estimates, in accordance with the disclosed embodiments.

FIG. 8 is a block diagram of an example computing system 800 that may be used to, for example, implement all or part of the machine learning model 202, the data transformer 208, the comparer 210, the ranker 228, the data collector 602, the channel assigner 604, the intervention definer 606, the rules engine 608, the rules adjuster 610 and/or, more generally, the adherence analyzers 106, 200 and/or the intervention builders 114, 600. The computing system 800 may be, for example, a server, a personal computer, a workstation, a self-learning machine (e.g., a neural network), or any other type of computing device.

The computing system 800 includes a processor 802, a program memory 804, a RAM 806, and an input/output (I/O) circuit 808, all of which are interconnected via an address/data bus 810. It should be appreciated that although FIG. 8 depicts only one processor 802, the computing system 800 may include multiple processors 802. The processor 802 of the illustrated example is hardware, and may be a semiconductor based (e.g., silicon based) device. Example processors 802 include a programmable processor, a programmable controller, a graphics processing unit (GPU), a digital signal processor (DSP), an ASIC, a PLD, an FPGA, an FPLD, etc.

The program memory 804 may include any number and/or type(s) of non-transitory, volatile and/or non-volatile machine-readable storage medium, devices or disks storing software or machine-instructions that may be executed by the processor 802 to implement all or part of the machine learning model 202, the data transformer 208, the comparer 210, the ranker 228, the data collector 602, the channel assigner 604, the intervention definer 606, the rules engine 608, the rules adjuster 610 and/or, more generally, the adherence analyzers 106, 200 and/or the intervention builders 114, 600. However, different portions of the adherence analyzers 106, 200 and/or the intervention builders 114, 600 may be implemented by different computing systems such as the computing system 800. Modules, systems, etc. instead of and/or in addition to those shown in FIG. 8 may be implemented. The software or machine-readable instructions may be stored on separate non-transitory, machine-readable storage mediums, devices or disks, and/or at different physical locations.

Example memories 804, 814, 816 include any number or type(s) of volatile or non-volatile, non-transitory, machine-readable storage medium, devices or disks, such as a semi-conductor memories, magnetically readable memories, optically readable memories, an HDD, an SSD, a ROM (e.g., a ROM 816), a RAM (e.g., a RAM 814), a redundant array of independent disks (RAID) system, a cache, a flash memory, or any other storage medium, device or disk in which information may be stored for any duration (e.g., permanently, for an extended time period, for a brief instance, for temporarily buffering, for caching of the information, etc.).

As used herein, the term non-transitory, machine-readable medium is expressly defined to include any type of machine-readable storage device and/or storage disk and to exclude propagating signals and to exclude transmission media.

In some embodiments, the processor 802 may also include, or otherwise be communicatively connected to, a database 812 or other data storage mechanism (one or more hard disk drives, optical storage drives, solid state storage devices, CDs, CD-ROMs, DVDs, Blu-ray disks, RAID, etc.). In the illustrated example, the database 812 may store any of the data 108, 110, 116, 118, 130, 134, 138, 140, 142, 144, 146, 214 and 224.

Although FIG. 8 depicts the I/O circuit 808 as a single block, the I/O circuit 808 may include a number of different types of I/O circuits or components that enable the processor 802 to communicate with peripheral I/O devices and/or other computing systems. Example interface circuits 808 include a universal serial bus (USB) interface, a Bluetooth® interface, a near field communication (NFC) interface, an infrared interface and/or a PCI express interface. The peripheral I/O devices may be any desired type of I/O device such as a keyboard, a display (a liquid crystal display (LCD), a cathode ray tube (CRT) display, a light emitting diode (LED) display, an organic light emitting diode (OLED) display, an in-place switching (IPS) display, a touch screen, etc.), a navigation device (a mouse, a trackball, a capacitive touch pad, a joystick, etc.), a speaker, a microphone, a printer, a button, a communication interface, an antenna, etc.

The I/O circuit 808 may include a number of different network transceivers 818 that enable the computing system 800 to communicate with other computing systems, such as the computing system 800, that implement other portions of the machine learning model 202, the data transformer 208, the comparer 210, the ranker 228, the data collector 602, the channel assigner 604, the intervention definer 606, the rules engine 608, the rules adjuster 610 and/or, more generally, the adherence analyzers 106, 200 and/or the intervention builders 114, 600 via, e.g., a network such as the Internet. The network transceiver 818 may be a wireless fidelity (Wi-Fi) transceiver, a cellular transceiver, an Ethernet network transceiver, an asynchronous transfer mode (ATM) network transceiver, a digital subscriber line (DSL) modem, a dialup modem, a satellite transceiver, a cable modem, etc.

Use of "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise. A device or structure that is "configured" in a certain way is configured in at least that way, but may also be configured in ways that are not listed.

Further, as used herein, the expressions "in communication," "coupled" and "connected," including variations thereof, encompasses direct communication and/or indirect communication through one or more intermediary components, and does not require direct mechanical or physical (e.g., wired) communication and/or constant communication, but rather additionally includes selective communication at periodic intervals, scheduled intervals, aperiodic intervals, and/or one-time events. The embodiments are not limited in this context.

Further still, unless expressly stated to the contrary, "or" refers to an inclusive or and not to an exclusive or. For example, "A, B or C" refers to any combination or subset of A, B, C such as (1) A alone, (2) B alone, (3) C alone, (4) A with B, (5) A with C, (6) B with C, and (7) A with B and with C. As used herein, the phrase "at least one of A and B" is intended to refer to any combination or subset of A and B such as (1) at least one A, (2) at least one B, and (3) at least one A and at least one B. Similarly, the phrase "at least one of A or B" is intended to refer to any combination or subset of A and B such as (1) at least one A, (2) at least one B, and (3) at least one A and at least one B.

Moreover, in the foregoing specification, specific embodiments have been described. However, one of ordinary skill in the art appreciates that various modifications and changes can be made in view of aspects of this disclosure without departing from the scope of the invention as set forth in the claims below. Accordingly, the specification and figures are to be regarded in an illustrative rather than a restrictive sense, and all such modifications made in view of aspects of this disclosure are intended to be included within the scope of present teachings.

Additionally, the benefits, advantages, solutions to problems, and any element(s) that may cause any benefit, advantage, or solution to occur or become more pronounced are not to be construed as a critical, required, or essential features or elements of any or all the claims.

Furthermore, although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

Finally, any references, including, but not limited to, publications, patent applications, and patents cited herein are hereby incorporated in their entirety by reference to the same extent as if each reference were individually and specifically indicated to be incorporated by reference and were set forth in its entirety herein.

The patent claims at the end of this patent application are not intended to be construed under 35 U.S.C. § 118(f) unless traditional means-plus-function language is expressly recited, such as "means for" or "step for" language being explicitly recited in the claim(s). The systems and methods described herein are directed to an improvement to computer functionality, and improve the functioning of conventional computers.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A computer-implemented method for estimating an adherence risk score for a medication taken by a patient, the method comprising:
   receiving, via a network interface from a server configured for determining follow up with patients regarding medication adherence, a request for an adherence risk score for a patient and medication combination, the adherence risk score representing a risk that the patient will not be adherent with taking the medication as prescribed during a time period;
   obtaining, with one or more processors,
      pharmacy records for the patient and medication combination, and
      data representing pharmacy records for the medication for a plurality of patients for a previous time period;
   training, with the one or more processors, a machine learning model, using the data, to determine the adherence risk score,
      wherein the machine learning model is a statistical machine learning model verified during training by computing a sum of squares metric to determine when the performance of the machine learning model is no longer improving;
   processing the pharmacy records with the machine learning model to determine the adherence risk score;
   providing, via the network interface, the adherence risk score to the server;
   obtaining, from one or more databases, updated data representing updated pharmacy records for the medication for a plurality of patients;
   obtaining, with one or more processors, updated medication adherence outcomes for a respective each patient of the plurality of patients representing whether they were adherent with their prescription for the medication;
   processing the updated data with the machine learning model to determine updated adherence risk scores for a respective each patient and medication combination;
   comparing, with the one or more processors, the updated medication adherence outcomes and the updated adherence risk scores for the respective each patient and medication combination for the plurality of patients;

updating the machine learning model based upon the comparison of the medication adherence outcome and the respective adherence risk score for the respective each patient and medication combination using predictive modeling; and processing the pharmacy records with the updated machine learning model upon receiving the request for the adherence risk score for the patient and medication combination.

2. The method of claim 1, wherein processing the pharmacy records includes inputting to the machine learning model at least one of a date of first fill for the medication during the time period, a number of refills during the time period, a number-of-days supply filled, a percentage of fills that were ninety day fills, a gap in prescriptions on hand, a number of refills remaining, or a copay amount.

3. The method of claim 1, further comprising obtaining, from the one or more databases, non-pharmacy records for the patient, wherein processing the pharmacy records includes processing the pharmacy records and the non-pharmacy records with the machine learning model to determine the adherence risk score.

4. The method of claim 1, further comprising obtaining, from the one or more databases, pharmacy records for other patients, wherein processing the pharmacy records includes processing the pharmacy records for the patient and the pharmacy records for other patients with the machine learning model to determine the adherence risk score.

5. The method of claim 1, further comprising obtaining, from the one or more databases, store records for a store at which the patient picks up prescriptions for the medication, wherein processing the pharmacy records includes processing the pharmacy records and the store records with the machine learning model to determine the adherence risk score.

6. The method of claim 5, wherein the store records includes non-prescription sales records.

7. The method of claim 5, wherein the store records include at least one of demographic information, socioeconomic information, or geographic information.

8. The method of claim 1, further comprising obtaining, from the one or more databases, response data representing responsiveness of the patient to electronic follow up, wherein processing the pharmacy records includes processing the pharmacy records and the response data with the machine learning model to determine the adherence risk score.

9. The method of claim 1, wherein training the machine learning model comprises:
obtaining, with the one or more processors, medication adherence outcomes for respective ones of the patients representing whether they were adherent with their prescription for the medication for the previous time period;
training the machine learning model with a first portion of the data based on comparisons of adherence risk scores determined by the machine learning model and respective ones of the medication adherence outcomes to form a trained machine learning model; and
validating the machine learning model with a second portion of the data based on comparisons of adherence risk scores determined by the trained machine learning model and respective ones of the medication adherence outcomes.

10. The method of claim 1, wherein the statistical machine learning model includes at least one of a multinomial logistic regression model, a decision tree, a gradient boost model, or a logistic regression model.

11. The method of claim 1, wherein the medication is for a targeted therapeutic class.

12. A system for estimating an adherence risk score for a medication taken by a patient, the system comprising:
a network interface configured to
receive from a server configured for determining follow up with patients regarding medication adherence, a request for an adherence risk score for a patient and medication combination, the adherence risk score representing a risk that the patient will not be adherent with taking the medication as prescribed during a time period,
provide the adherence risk score to the server, and
provide one or more files to one or more respective interaction systems;
a data transformer configured to
obtain pharmacy records for the patient and medication combination;
obtain updated data representing updated pharmacy records for the medication for a plurality of patients; and
obtain updated medication adherence outcomes for a respective each patient of the plurality of patients representing whether they were adherent with their prescription for the medication;
a machine learning model configured to
process the pharmacy records to determine the adherence risk score; and
process the updated data to determine updated adherence risk scores for a respective each patient and medication combination;
an intervention builder configured to
select one or more interaction systems to contact the patient regarding the medication adherence, wherein the one or more interaction systems are different types of interaction systems, and the selection is based at least upon the risk adherence risk score of the patient,
generate a respective file for each selected interaction system, wherein the file includes information to contact the patient regarding the medication adherence, and
provide, via the network interface to the each selected interaction system, the respective file;
a comparer configured to
compare the updated medication adherence outcomes and the updated adherence risk scores for the respective each patient and medication combination for the plurality of patients; and
the machine learning model further configured to
update the machine learning model based upon the comparison of the medication adherence outcome and the respective adherence risk score for the respective each patient and medication combination; and
process the pharmacy records with the updated machine learning model upon receiving the request for the adherence risk score for the patient and medication combination.

13. The system of claim 12, wherein
the data transformer is configured to obtain data representing at least one of non-pharmacy records for the patient, pharmacy records for other patients, non-prescription sales records, demographic information for a store, socioeconomic information for a store, or geographic information for the store, and the machine learning model is configured to process the pharmacy records and the obtained data with the machine learning model to determine the adherence risk score.

14. The system of claim 12, wherein the pharmacy records include at least one of a date of first fill for the medication during the time period, a number of refills during the time period, a number-of-days supply filled, a percentage of fills that were ninety day fills, a gap in prescriptions on hand, a number of refills remaining, or a copay amount.

15. The system of claim 12, wherein:
the data transformer is configured to
obtain data representing pharmacy records for the medication for a plurality of patients for a previous time period,
obtain medication adherence outcomes for respective ones of the patients representing whether they were adherent with their prescription for the medication for the previous time period; and
the machine learning model is configured to
train the machine learning model with a first portion of the data based on comparisons, by the comparer, of adherence risk scores determined by the machine learning model and respective ones of the medication adherence outcomes to form a trained machine learning model; and
validate the machine learning model with a second portion of the data based on comparisons, by the comparer, of adherence risk scores determined by the trained machine learning model and respective ones of the medication adherence outcomes.

16. The system of claim 12, wherein the one or more interaction systems include one or more of an interactive voice response system, a digital communication system, or a pharmacy system.

17. The system of claim 12, wherein at least one selected interaction system contacts the patient using the respective file.

18. A non-transitory, machine-readable storage medium comprising instructions that, when executed by one or more processors, cause a machine to:
receive, via a network interface from a server configured for determining follow up with patients regarding medication adherence, a request for an adherence risk score for a patient and medication combination, the adherence risk score representing a risk that the patient will not be adherent with taking the medication as prescribed during a time period;
obtain pharmacy records for the patient and medication combination, and data representing pharmacy records for the medication for a plurality of patients for a previous time period;
train a machine learning model using the data to determine the adherence risk score,
wherein the machine learning model is a statistical machine learning model verified during training by computing a sum of squares metric to determine when the performance of the machine learning model is no longer improving;
process the pharmacy records with the machine learning model to determine the adherence risk score;
provide, via the network interface, the adherence risk score to the server
obtain updated data representing updated pharmacy records for the medication for a plurality of patients;
obtain updated medication adherence outcomes for a respective each patient of the plurality of patients representing whether they were adherent with their prescription for the medication;
process the updated data with the machine learning model to determine updated adherence risk scores for a respective each patient and medication combination;
compare the updated medication adherence outcomes and the updated adherence risk scores for the respective each patient and medication combination for the plurality of patients;
update the machine learning model based upon the comparison of the medication adherence outcome and the respective adherence risk score for the respective each patient and medication combination; and
processing the pharmacy records with the updated machine learning model upon receiving the request for the adherence risk score for the patient and medication combination.

19. The non-transitory, machine-readable storage medium of claim 18, wherein the instructions, when executed by one or more processors, cause the machine to obtain data representing at least one of non-pharmacy records for the patient, pharmacy records for other patients, non-prescription sales records, demographic information for a store, socioeconomic information for a store, or geographic information for the store, wherein processing the pharmacy records includes processing the pharmacy records and the obtained data with the machine learning model to determine the adherence risk score.

20. The non-transitory, machine-readable storage medium of claim 18, wherein the instructions, when executed by one or more processors, cause the machine to:
obtain medication adherence outcomes for respective ones of the patients representing whether they were adherent with their prescription for the medication for the previous time period;
train the machine learning model with a first portion of the data based on comparisons of adherence risk scores determined by the machine learning model and respective ones of the medication adherence outcomes to form a trained machine learning model; and
validate the machine learning model with a second portion of the data based on comparisons of adherence risk scores determined by the trained machine learning model and respective ones of the medication adherence outcomes.

* * * * *